(12) United States Patent
Riitano

(10) Patent No.: US 7,980,853 B2
(45) Date of Patent: Jul. 19, 2011

(54) METHODS FOR APICAL PREPARATION USING ENDODONTIC INSTRUMENTS MADE OF SUPER-ELASTIC ALLOYS

(75) Inventor: Francesco Riitano, Soverato (IT)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 11/175,239

(22) Filed: Jul. 6, 2005

(65) Prior Publication Data
US 2007/0009850 A1  Jan. 11, 2007

(51) Int. Cl.
*A61C 5/02* (2006.01)
(52) U.S. Cl. .................................................. 433/224
(58) Field of Classification Search ............... 433/102, 433/81, 224
See application file for complete search history.

(56) References Cited

U.S. PATENT DOCUMENTS

| | | | |
|---|---|---|---|
| 3,578,745 A * | 5/1971 | Garnier et al. | 433/102 |
| 4,544,356 A | 10/1985 | Gardella et al. | |
| 4,611,508 A * | 9/1986 | Roane | 76/24.1 |
| 4,889,487 A | 12/1989 | Lovaas | |
| 5,380,200 A * | 1/1995 | Heath et al. | 433/102 |
| 5,653,590 A * | 8/1997 | Heath et al. | 433/102 |
| 5,857,852 A * | 1/1999 | Garman | 433/102 |
| 5,915,964 A | 6/1999 | Walia | |
| 5,938,440 A | 8/1999 | McSpadden | |
| 6,217,335 B1 * | 4/2001 | Riitano et al. | 433/224 |
| 6,293,795 B1 | 9/2001 | Johnson | |
| 6,390,819 B2 | 5/2002 | Riitano | |
| 6,431,863 B1 | 8/2002 | Sachdeva et al. | |
| 6,520,774 B1 | 2/2003 | Mays | |
| 6,585,513 B2 | 7/2003 | Fischer | |
| 6,746,245 B2 | 6/2004 | Riitano et al. | |
| 2001/0016309 A1 * | 8/2001 | Riitano | 433/224 |
| 2002/0137008 A1 | 9/2002 | McSpadden et al. | |
| 2003/0211442 A1 * | 11/2003 | Abel | 433/102 |
| 2004/0058298 A1 | 3/2004 | Brava et al. | |
| 2004/0121283 A1 * | 6/2004 | Mason | 433/102 |

OTHER PUBLICATIONS

Riitano, F., Anatomic Endodontic Technology (AET)—a crown-down root canal preparation technique: basic concepts operative procedure and instruments; International Endodontic Journal, vol. 38, pp. 575-587 (2005).
Serota, K. et al., Predictable Endodontic Success: The Hybrid Approach—Part I—Oral Health, vol. 93(5), pp. 41-48 (2003).
Serota, K. et al., Predictable Endodontic Success: Part II—Microstructural Replication—Oral Health, vol. 12(93), pp. 36-41 (2003).
Ponti, T. et al., Canal-centering ability of two rotary file systems, J. Endod., vol. 28(4), pp. 283-286 (Apr. 2002).

* cited by examiner

*Primary Examiner* — Cris L Rodriguez
*Assistant Examiner* — Sunil K Singh
(74) *Attorney, Agent, or Firm* — Workman Nydegger

(57) ABSTRACT

The apical third of a root canal is cleaned and/or shaped during a root canal procedure with an endodontic file made from a titanium-based alloy either by reciprocating manual use or by using a reciprocating powered hand piece. The titanium-based endodontic file has super-elastic properties that allow it to be very flexible and strong. The endodontic file is rotated in the apex of a root canal in degrees of rotation less than 120 degrees. By restricting the degree of rotation, excessive cutting by the endodontic file is kept to a minimum. The use of elastic alloys of titanium help prevent ledging or other damage to the root canal wall that may be caused using rigid apical files made of stainless steel.

26 Claims, 12 Drawing Sheets

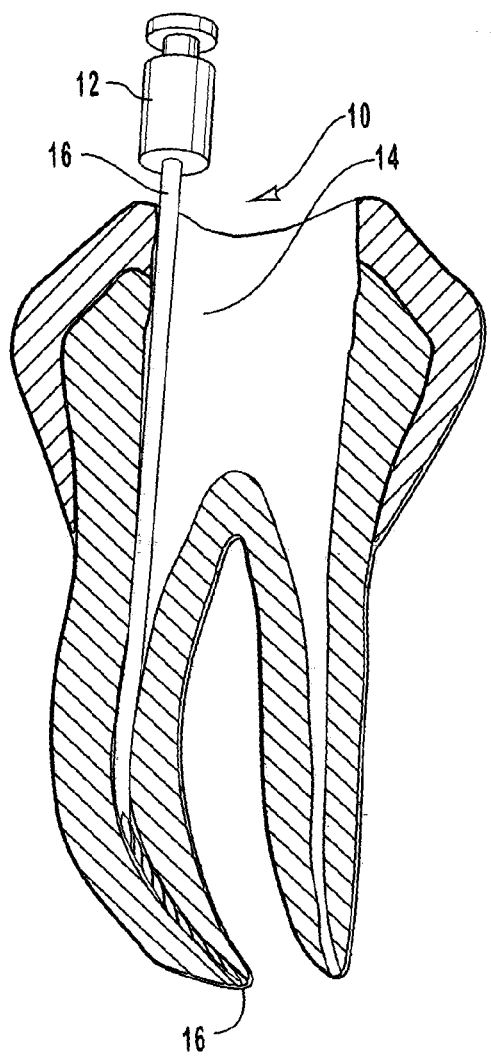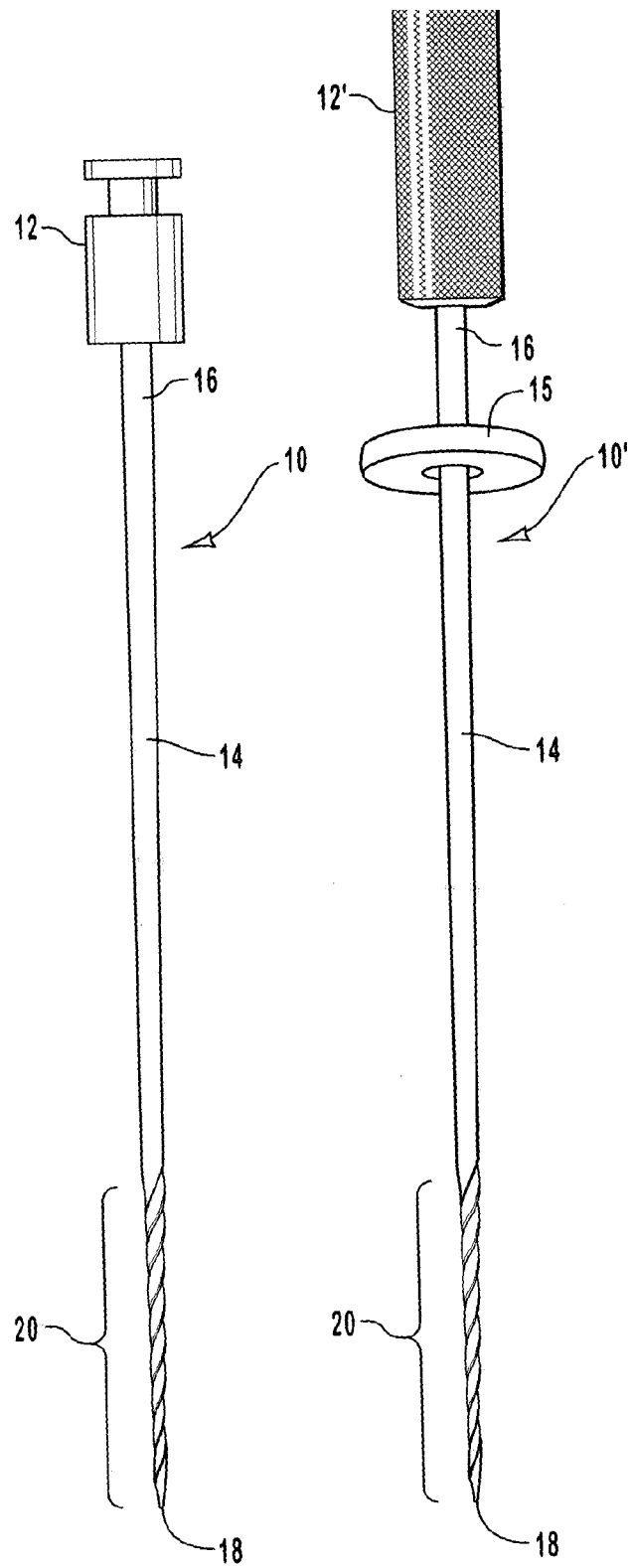
FIG. 1
FIG. 2A
FIG. 2B

METHODS FOR APICAL PREPARATION USING ENDODONTIC INSTRUMENTS MADE OF SUPER-ELASTIC ALLOYS

BACKGROUND OF THE INVENTION

1. The Field of the Invention

The present invention relates to procedures for using an endodontic instrument to prepare a root canal of a tooth for receiving a sealer or filler material. More particularly, the invention relates to a method of using a super-elastic apical endodontic file either manually or in a reciprocating hand piece.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material that forms the nerve of the tooth, which has become infected. After careful preparation of the canal that contained the nerve material the canal is refilled with an inert filling material, such as gutta percha. This process allows the patient to retain the tooth.

To achieve a successful root canal restoration, the dental practitioner must carefully and, as completely as possible, remove the infected pulp material. The removal process typically includes shaping the root canal so that it can be effectively and successfully filled and sealed with an inert material to reduce the possibility of further infection.

Cleaning and shaping the root canal in preparation of receiving a sealing or filling material is achieved by the use of metal files that include cutting surfaces for removing tissue in the root canal. The cutting surfaces are typically formed by helical flutes formed in the file. Some existing endodontic instruments and manufacturing methods are described in U.S. Pat. No. 4,934,934; U.S. Pat. No. 5,653,590; and U.S. Pat. No. 5,762,541.

Since root canals are seldom straight, often having bends and twists, at least some endodontic files are advantageously flexible. Currently preferred materials of construction include stainless steel, and more recently, nickel-titanium (Ni—Ti) alloys.

Endodontic files made from super-elastic materials such as Ni—Ti alloys have been found to be particularly useful for cleaning a root canal because they exhibit good flexibility, resilience and strength, and are not likely to fail during use. Flexibility and strength are important to avoid file breakage during the cleaning process.

As mentioned above, endodontic files typically have a helical or similar cutting edge along the length of the file. An endodontic file is used to remove tissue from the root canal by turning (i.e., twisting) the file within the root canal and/or moving the file up and down in the root canal.

The turning motion of the endodontic file in a root canal can be accomplished by hand or alternatively, by a powered hand piece. Hand manipulated endodontic files have a handle on the end that gives the practitioner the ability to grip and manipulate the file as desired. An endodontic file used in a powered hand piece has a chuck on one end for placing the file in the powered hand piece. The advantage of a powered hand piece is that it can be easier and quicker for a practitioner to use.

One problem with some rotating powered hand pieces is that once the cutting edge catches on the tissue and begins cutting, the cutting edge can sometimes dig in and remove excessive amounts of tissue. To overcome the problem with "digging in," some powered hand pieces reciprocate. A reciprocating hand piece oscillates back and forth, thereby preventing excessive cutting from the cutting edge digging in.

While a reciprocating hand piece provides a significant advantage for conveniently removing tissue in the root canal, the use of a reciprocating hand piece has been somewhat limited with endodontic files made from super-elastic materials. In particular, apical endodontic files made of super-elastic materials are currently not used in reciprocating hand pieces. On the other hand, using a rigid apical file made from stainless steel with a reciprocating handpiece in inadvisable since the tip of the rigid apical file can bore right into the root canal wall and/or cause what is know as "ledging".

Apical files are used to clean the apical third of the tooth. Cleaning this portion of the root canal can be more technical because of the narrow spaces in the apex and the delicateness of the apex and apical files. Apical files are more susceptible to breaking and their breakage is more difficult to remedy. Furthermore because apical files are long and thin, they are more flexible than files used to clean other portions of the root canal. The flexibility of apical files made from super-elastic materials is such that the files have a tendency to simply wind and unwind as they are reciprocated in a reciprocating handpiece. Winding and unwinding decreases the cutting effect of the reciprocating file and increases the risk that the apical file will break. Consequently, apical endodontic files made from super-elastic materials such as NiTi are only used in a powered hand piece that rotates in only one direction.

Therefore, what is needed is a method of using an apical file made from a super-elastic material either manually or with a powered hand piece that minimizes the effects of winding and unwinding and reduces the risk that the apical file will break during use in the apex.

BRIEF SUMMARY OF THE INVENTION

The present invention provides improved methods for cleaning the apical portion of a root canal of a tooth. The present invention includes using a super-elastic apical endodontic file either manually or in a reciprocating powered hand piece to clean the apical portion of a root canal. The apical endodontic file is sized and configured to be placed into the apical portion of a root canal of a tooth. The apical file is also made of a titanium-based material having super-elastic properties. The tissue in the apical portion of the root canal is cut and removed by reciprocating the apical file back and forth in the root canal either manually or by using a powered hand piece.

In an exemplary embodiment, a powered hand piece or manual manipulation (i.e., a practitioner's hand) is used to reciprocate the apical file back and forth in degrees of rotation less than about 60 degrees for a total of about 120 degrees of rotation. In a more preferred embodiment, the total degrees of rotation are less than about 90 degrees, more preferably less than about 80 degrees, even more preferably less than about 70 degrees, and most preferably less than about 60 degrees.

The apical files of the present invention are made from titanium based materials having super-elastic properties. Because the apical files are made from these materials, the apical files have superior flexibility and hardness. This flexibility allows the apical files to better shape the contours of a person's root canal. The greater flexibility also reduces the risk of ledging. Ledging can occur in root canals that have a substantial degree of curvature, particularly when more rigid files are used (e.g., made from stainless steel).

In an exemplary embodiment, the material used to form the apical files includes large percentages of nickel and titanium.

In one embodiment, the titanium content of a nickel-titanium alloy is between about 20% and about 80%, more preferably between about 30% and about 70%, and most preferably between about 40% and about 60%.

In yet another embodiment, the material used to form the apical files includes at least one group IV transition metal, at least one group V transition metal, and oxygen. Examples of suitable materials meeting these criteria include metal alloys having a composition in mole percent of 1Ti-12Ta-9Nb-3V-6Zr-1O or 1Ti-23Nb-0.7Ta-2Zr-1O.

Although super-elastic materials are very flexible, surprisingly, the inventors of the present invention have found that super-elastic apical files can be used in a reciprocating manner (e.g., either manually or in a reciprocating powered hand piece) while still obtaining sufficient cutting of root canal tissue. In an exemplary embodiment, restricting the degrees of rotation according to the present invention avoids the problems associated with using super-elastic based apical files in a reciprocating manner. For example, apical files rotated with restricted degrees of rotation are less likely to cut excessively or break. Surprisingly, restricting rotation does not significantly impair the cutting ability of the apical file.

Cleaning the apical portion of a root canal using the methods of the present invention can be done more quickly and efficiently. These advantages reduce the time and expense associated with performing an endodontic procedure using titanium-based files.

These and other benefits, advantages, and features of the present invention will become more fully apparent from the following description and appended claims.

BRIEF DESCRIPTION OF THE DRAWINGS

A more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1 is a cross sectional view of a tooth having two roots, with an endodontic instrument being positioned in one of the roots;

FIGS. 2A-2B illustrate exemplary endodontic instruments used in exemplary methods of the present invention;

DETAILED DESCRIPTION OF EXEMPLARY EMBODIMENTS

I. Introduction

Figure 3A:
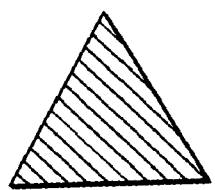
FIGS. 3A-3J show cross sections of various exemplary endodontic instruments used in the method of the present invention.
Figure 3B:
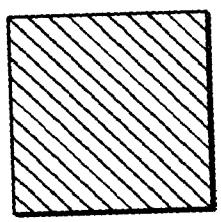
Figure 3C:
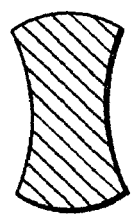
Figure 3D:
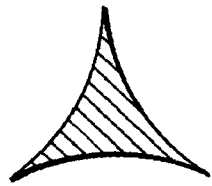
Figure 3E:
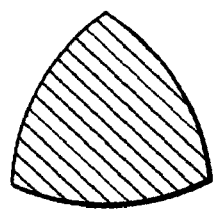
Figure 3F:
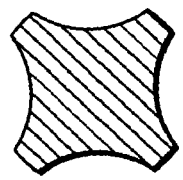
Figure 3G:
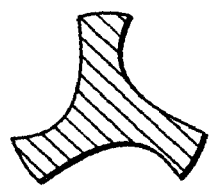
Figure 3H:
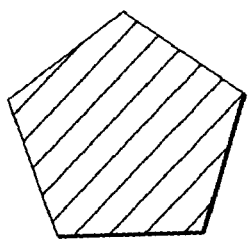
Figure 3I:
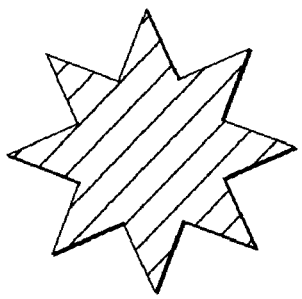
Figure 3J:
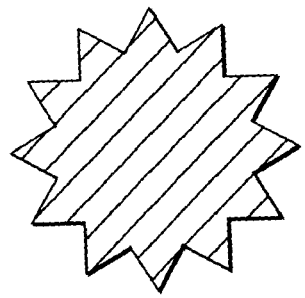

The present invention relates to methods for cleaning the apical portion of a root canal using an apical endodontic file made from a super-elastic material such as NiTi or "gum metal." The method includes providing an apical file configured for cutting tissue in the apical portion of a root canal, inserting the apical file into the root canal, and cutting tissue in the apical portion of the root by reciprocating the apical file (e.g., either manually or by using a powered hand piece).

II. Exemplary Apical Files

FIGS. 1 and 2A show an exemplary apical file 10 configured and designed for cutting and cleaning pulp material from the apical portion of a root canal. Apical file 10 includes a chuck 12 connected to a shaft 14. Apical file 10 has a top end 16 where the file joins chuck 12 and terminates at a tip 18 located opposite top end 16.

Tip 18 can have any configuration; however, tip 18 preferably has minimal cutting capability to decrease the likelihood of ledging. An example of a suitable configuration for tip 18 is a rounded tip, an example of which is illustrated close up in FIG. 4.

Apical file 10 is configured to have an abrading portion 20 along at least a portion of the length of shaft 14. Abrading portion 20 preferably extends from tip 18 part way upward towards top end 16 such that the remainder of file 10 is relatively smooth. More particularly, apical file 10 is preferably configured with an abrading portion along less than about half of the length of the file, and more preferably about one-third of the length between tip 18 and top end 16.

The length of an apical file, such as apical files 10, is sufficient such that when the apical file is inserted into the root canal, the tip can at least approximately reach the apex, and the abrading portion 20 of the file can substantially contact and clean the pulp material in the apical portion of the root canal, as discussed more fully below. Such file lengths are typically within a range from about 8 mm to about 35 mm, more preferably in a range from about 14 mm to about 35 mm, and most preferably in a range from about 12 mm to about 33 mm. The length of the abrading portion is generally within a range from about 1 mm to about 35 mm, more preferably in a range from about 2 mm to about 16 mm, and most preferably in a range from about 3 mm to about 6 mm. The diameter of abrading portion 20 is generally within a range from about 0.06 mm to about 1.4 mm.

FIG. 2B illustrates an alternative apical endodontic file 10' configured for manual use. Apical endodontic file 10' includes a handle 12', a shaft 14, a top end 16, a tip 18, and an abrading portion 20. Handle 12' is configured to be gripped by a practitioner during manual use. Apical endodontic file 10' may also include a rubber stopper 15, which can be used in estimating the length of the root canal. Hatch markings on the file may alternatively be included for this purpose.

The files used to clean the apical root portion can be designed for primarily longitudinal movement, rotational movement or combinations thereof. The apical files are preferably sufficiently flexible to adjust to the anatomy or structure of a root canal in a manner that enables the tip of the file to reach the apex. The files also preferably have sufficient rigidity to apply pressure against the walls or surfaces of the root canal as the abrading portion of the file is urged against the walls of the root canal and simultaneously moved in a cleaning motion. An apical file preferably has adequate resilience to avoid being substantially deformed as the file passes through a root canal and also as the abrading portion is urged against the walls of the root canal. Although FIG. 1 illustrates use of apical endodontic file 10, it is to be understood that apical endodontic file 10' could alternatively be used.

Figure 4:
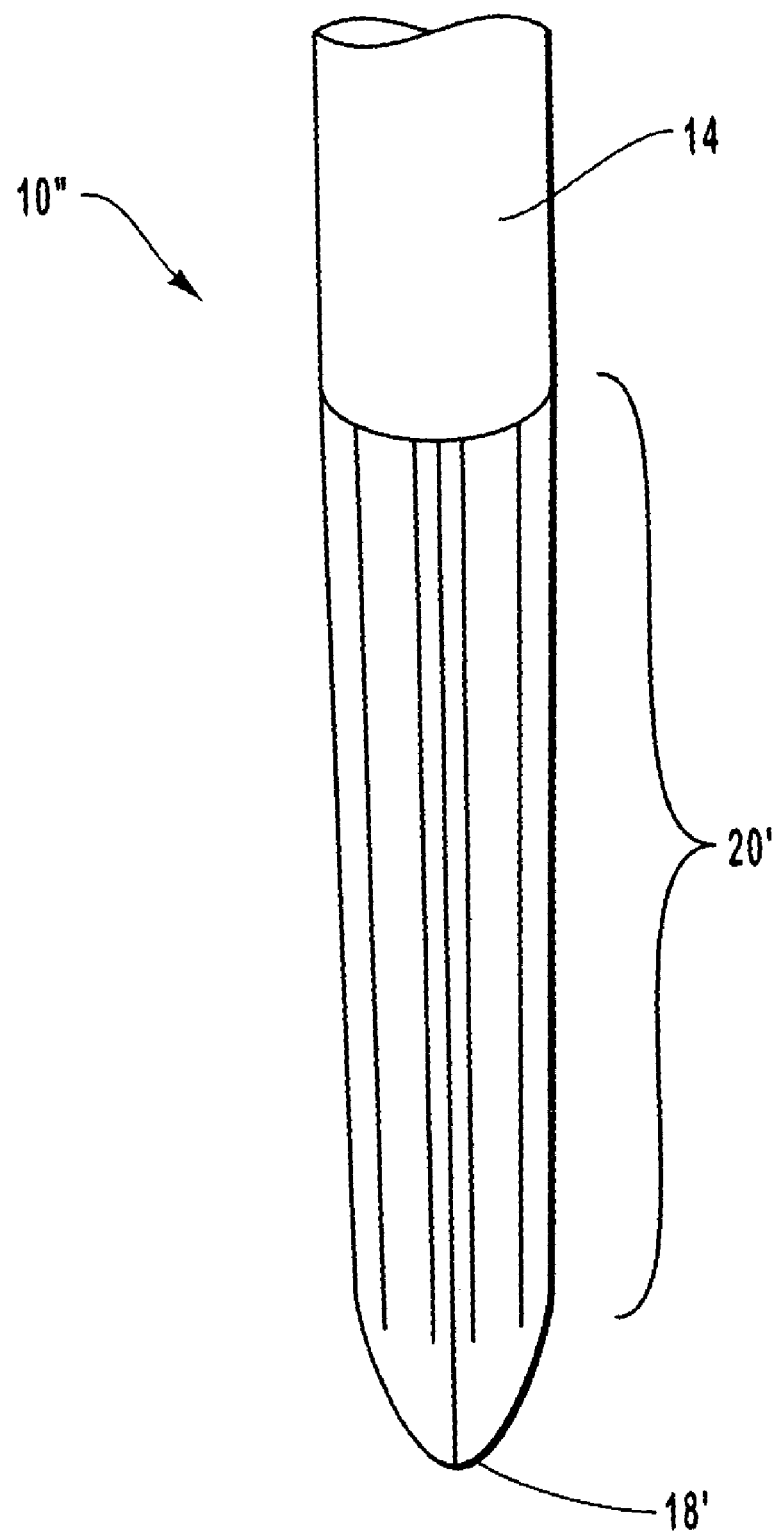
FIG. 4 illustrates one preferred exemplary endodontic instrument having the cross section illustrated in FIG. 3I.

FIGS. 3A-3J are transverse cross-sections of exemplary apical files that can be utilized to clean the apical root portion of the root canal. The transverse cross-section shows different exemplary abrading portions for each apical file. In an exemplary embodiment, abrading portion 20 of apical file 10 is formed by twisting a blank having a polygonal cross section. In a one embodiment, the abrading portion 20 preferably has few spirals such that the action of abrading portion 20 against the walls or surfaces of the apical portion of the root canal is relatively gentle. Such an abrading portion is less aggressive, as fewer spirals result in tines that have a wider angle. However, the number of abrading edges may be increased as the degree of rotation of apical file 10 (or 10') is reduced, as discussed more fully below. FIG. 4 illustrates a close up perspective view of one preferred apical endodontic file 10" having the cross section of FIG. 3I.

Conventional file designs can also be utilized within the scope of the present invention. Accordingly, the files are not limited to the designs shown in FIGS. 3A-3J. The files, however, are preferably configured in a manner such that the potential for breakage is minimized. All of the files, in combination with their respective abrading portions disclosed herein, are examples of means for abrading a root canal.

Apical files 10, 10', and 10" are formed from a titanium-based material having super-elastic properties. Super-elastic alloys have a low elastic modulus and high strength, which is uncharacteristic of most metals. Suitable super-elastic materials that can be used to make apical files include nickel-titanium alloys (Ni—Ti), nickel-titanium-chromium alloys, nickel-titanium-copper alloys, nickel-titanium-niobium alloys, and other super-elastic materials.

Although any suitable super-elastic metallic material may be used, nickel-titanium alloys are preferred because they are strong yet flexible and resilient. The Ni—Ti alloy preferably has a titanium content in a range of about 20% to about 80%, more preferably in a range of about 30% to about 70%, and most preferably in a range of about 40% to about 60%. In one embodiment, the balance of the alloy may comprise nickel and small amounts of other ingredients that do not adversely affect the suitability of the material for use as an endodontic instrument.

In an alternative embodiment, the apical files are made from titanium-based alloys comprising atoms selected from group IV and V transition metals and oxygen, which are also referred to as "gum metal." In one embodiment, the super-elastic alloys contain combinations of titanium (Ti), zirconium (Zr), tantalum (Ta), niobium (Nb), vanadium (V), and hafnium (Hf). In a preferred embodiment, titanium is included in a molar concentration of less than about 35 mole percent, more preferably less than about mole percent, and most preferably less than about 5 mole percent.

If present, oxygen (O) is included in a concentration of about 0.1 to about 15 mole percent. More preferably, oxygen concentration is about 0.5 to about 10 mole percent and even more preferably between about 0.7 to about 4 mole percent. It is believed that oxygen is important for binding to zirconium to form Zr—O clusters that prevent dislocation activity, thus creating plasticity in the cold worked metal.

The super-elastic metal alloys formed from group IV and group V transition metals are formed by combining group IV and group V transition metals and oxygen in particular mole ratios. Mole concentrations are selected such that the metal alloys have the following characteristics: (i) a compositional average valence electron number of about 4.24; (ii) a bond order of about 2.87; and (iii) a "d" electron-orbital energy level of about 2.45 eV. Examples of alloy compositions that satisfy the above mentioned properties include alloys having formulas of 1Ti-12Ta-9Nb-3V-6Zr-1O and 1Ti-23Nb-0.7Ta-2Zr-1O (mole percent). Additional details regarding the formation and properties of "gum metal" are described in applicant's co-pending U.S. Provisional Patent Application Ser. No. 60/586,738, filed on Jul. 9, 2004 and entitled "Dental Abrading Instruments Made From Super-elastic Alloys," which is incorporated herein by reference.

III. Method of Cleaning Apical Portion of a Root Canal

The apical files can be used according to the present invention to clean the apical third of a root canal using various methods, including the coronal-apical method or the apical-coronal method. The following exemplary methods according to the present invention follow the coronal-apical or top down method.

Figure 5:
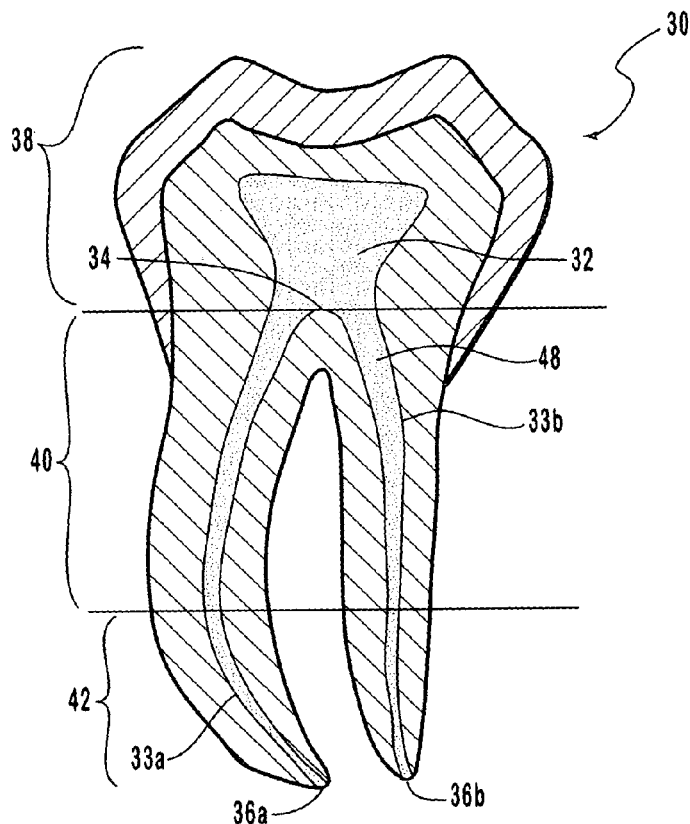
FIG. 5 illustrates a cross section of a tooth, showing exemplary divisions of the coronal, middle, and apical thirds of the tooth.

In an exemplary embodiment, a root canal is cleaned in progressive sections from crown to apex. The root canal is typically prepared in three phases, which correspond with three sections or portions of the operative root canal. FIG. 5 shows tooth 30 illustrating the divisions between the three portions of the tooth.

As seen in FIG. 5, pulp chamber 32 is connected to anatomical root canals 33a and 33b (collectively referred to as "anatomical root canal 33"). The operative root canal is considered to include the anatomical root canal 33, which extends from the floor 34 of the pulp chamber 32 to the apexes 36a and 36b (collectively referred to as "apex 36"), and the portion thereabove. More specifically, the operative root canal comprises the operative coronal portion 38, the operative middle portion 40, and the apical portion 42. Operative coronal portion 38 essentially includes the access cavity walls. The operative middle portion 40 is the upper portion of the anatomical root canal 33, while the apical portion 42 is the lower portion of the anatomical root canal 33.

Typically, the length of the apical portion 42 is less than half of the length of the anatomical root canal 33, as measured from the apex 36 to floor 34. More specifically, apical portion 42 is generally the bottom one-third of the anatomical root canal 33. The actual length of the apical portion 42 varies depending on many factors, such as the type of tooth and the age of the tooth. However, the apical portion 42 typically has a length in a range from about 3 mm to about 4 mm as measured from the apex 36.

As indicated above, the middle portion 40 is the top portion of the anatomical root canal 33 and extends from floor 34 down to an area of anatomical root canal 33, such that the length of the operative middle portion is greater than half of the length of anatomical root canal 33. More specifically, operative middle portion 40 is generally the top two-thirds of anatomical root canal 33 as measured down from floor 34. The length of the operative middle portion can be estimated by identifying the overall length of the root canal, typically by use of radiography, and then subtracting about 3 mm to 4 mm from the overall length.

As previously indicated, the three sections are treated in three primarily distinct sequential phases including: preparation of the operative coronal portion; cleaning the operative middle portion; and cleaning the apical portion.

Figure 6:
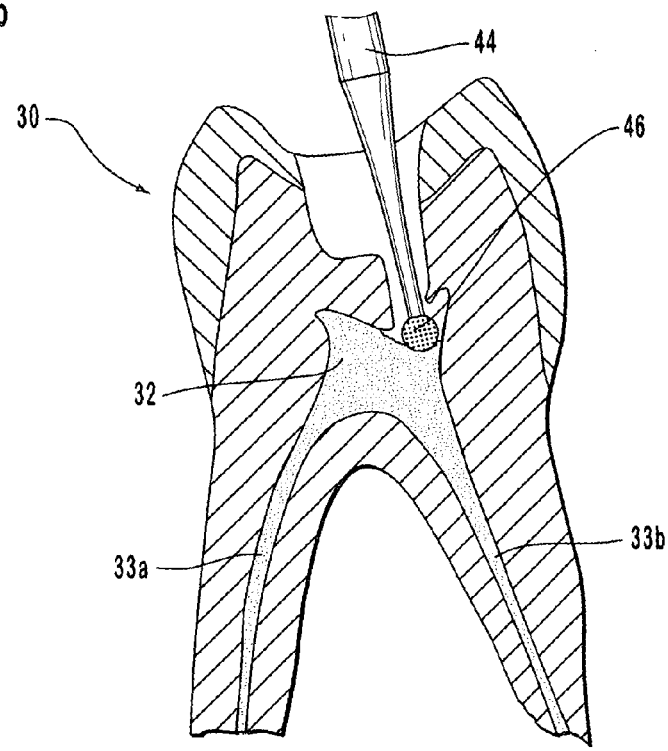
FIG. 6 illustrates a cross section of the tooth of FIG. 5 and an exemplary method for gaining access to the root canal.
Figure 7A:
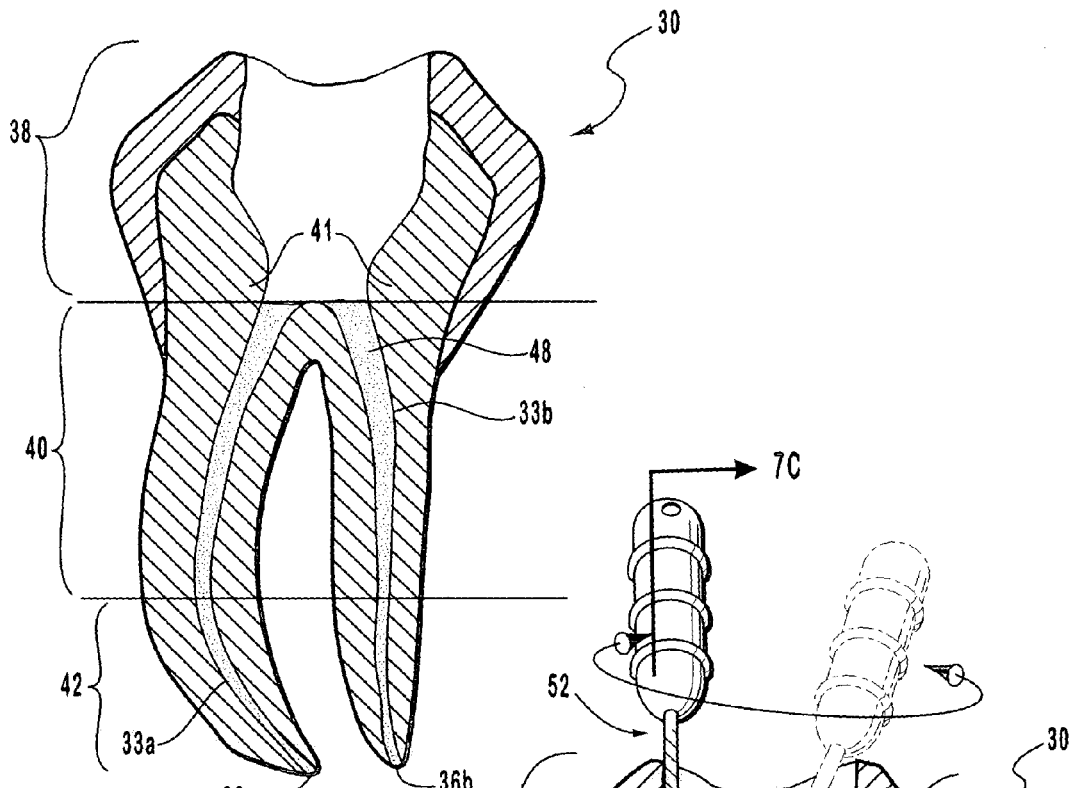
FIGS. 7A-7E illustrate cross sections of the tooth of FIG. 5, illustrating cleaning of the middle third of the tooth using an endodontic instrument.

The first phase, or "coronal phase," involves exposing the pulp chamber and also preferably other steps to enhance accessibility into operative middle portion 40 and also apical portion 42. Accordingly, the coronal or "access" phase is initiated by exposing the pulp chamber. This can be achieved, for example, through the use of an instrument such as instrument 44 with bur 46 as shown in FIG. 6. After pulp chamber 32 has been properly exposed and the pulp material removed, the tooth appears as shown in FIG. 7A, further described below. Pulp material 48 still extends within root canals 33a and 33b from apices 36a and 36b to the floor 34 of pulp chamber 32.

After the operative coronal portion has been adequately prepared, it is preferable to prepare an X ray image of the tooth to identify the length of the operative root canal for use in identifying the preferred working length for the endodontic instrument or set of endodontic instruments that are to be used in the middle portion 40 and apical portion 42. The preferred working length of an instrument for use in the middle portion 40 is preferably identified by subtracting about 3-4 mm from the total radiographic length of the operative root canal. The total radiographic length is preferably derived from a radiograph made using a localizator and a long cone radiographic head.

Figure 7B:
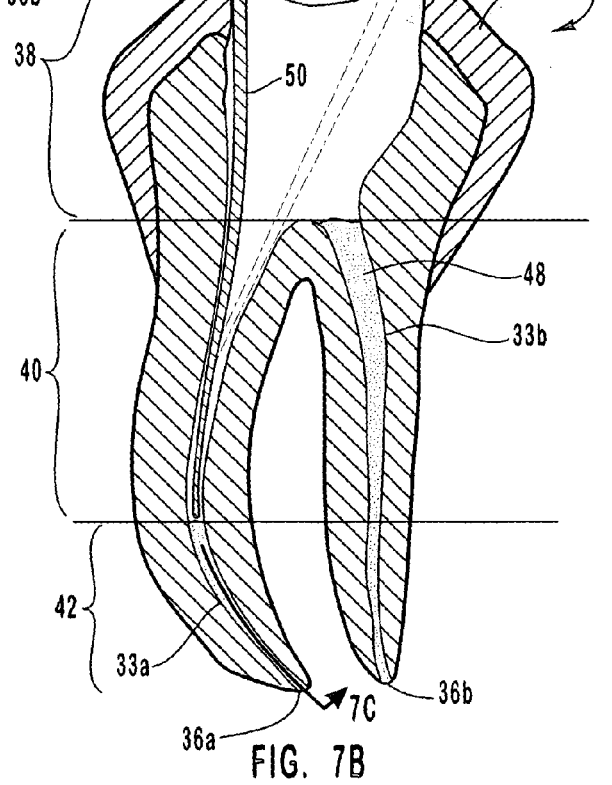
Figure 7C:
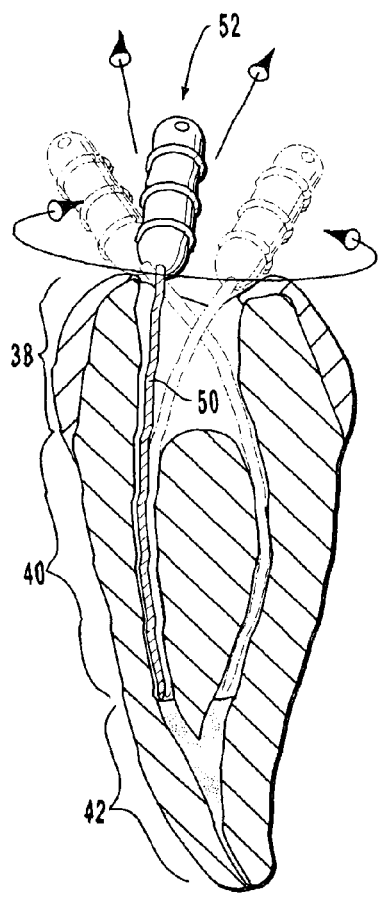
Figure 7D:
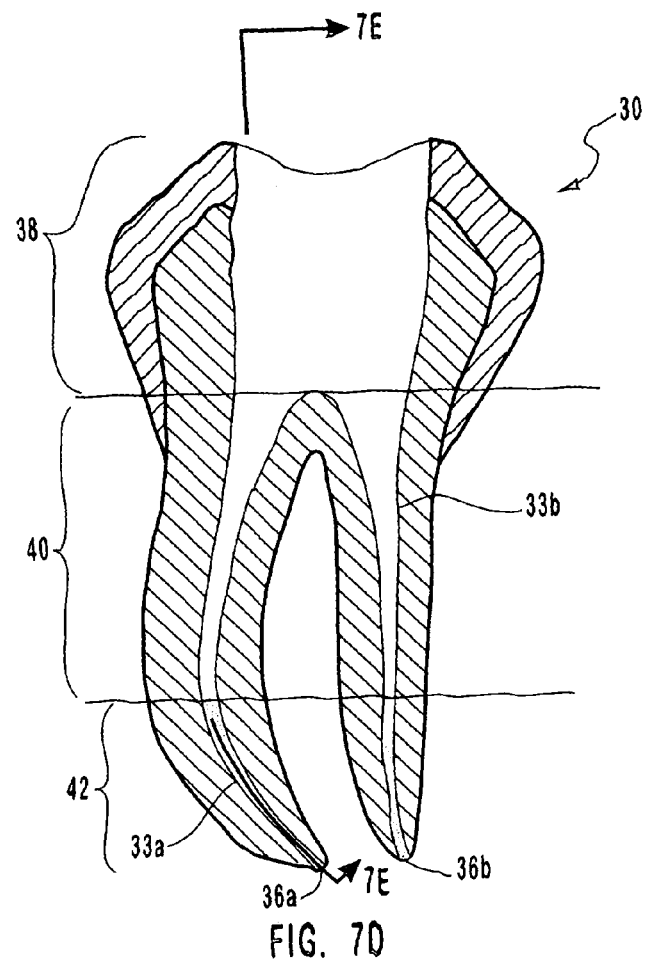
Figure 7E:
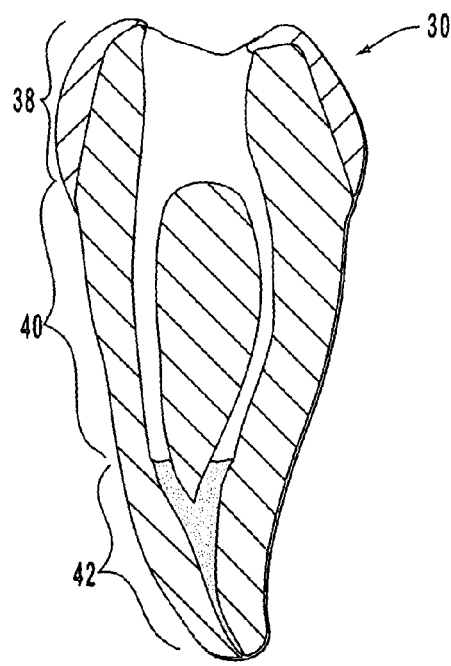

After identifying the operative middle portion length, the practitioner selects a file instrument or a set of file instruments with a file length corresponding to the operative middle portion length. The length of each file used to clean the operative middle portion depends on the tooth being cleaned. However, the length is generally in a range from about 8 mm to about 35 mm. As shown in FIG. 7B, file 50 of file instrument 52 is then inserted into root canal 33a down through operative middle portion 40 without extending substantially into apical portion 42. Endodontic instrument 52 is used to remove and clean essentially all pulp material from the operative middle portion 40 without significantly removing pulp material from the apical root portion 42. Although FIG. 7B illustrates use of a file configured for manual use, a file configured for use with a powered hand piece can alternatively be used to rotate or reciprocate endodontic instrument 52 to remove the pulp in the middle portion 40 and to remove interferences 41. FIG. 7B illustrates a cross sectional view of the tooth. FIG. 7C illustrates the same tooth as 7B, taken along cutting line 7C. FIG. 7D illustrates the tooth and cross sectional view of FIG. 7B after cleaning of the middle portion 40 is complete. FIG. 7E illustrates the tooth of 7D, taken along cutting line 7D and showing the tooth after cleaning of the middle portion 40 is complete.

Figure 8A:
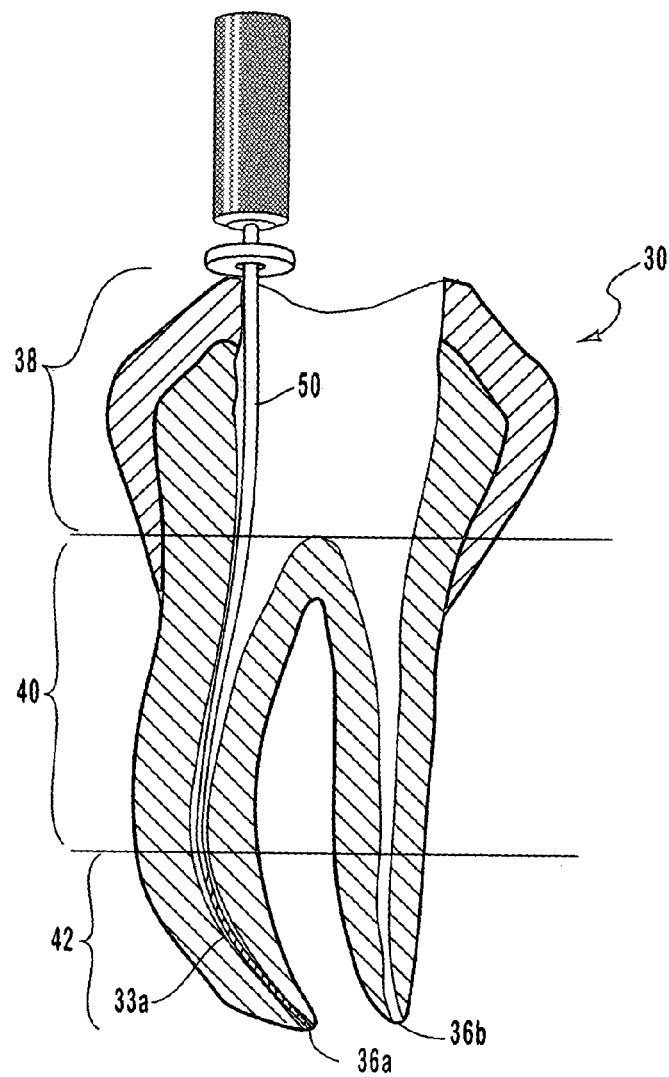
FIG. 8A illustrates manual cleaning and shaping of the apical third of the tooth of FIG. 7E according to one method of the present invention.
Figure 8B:
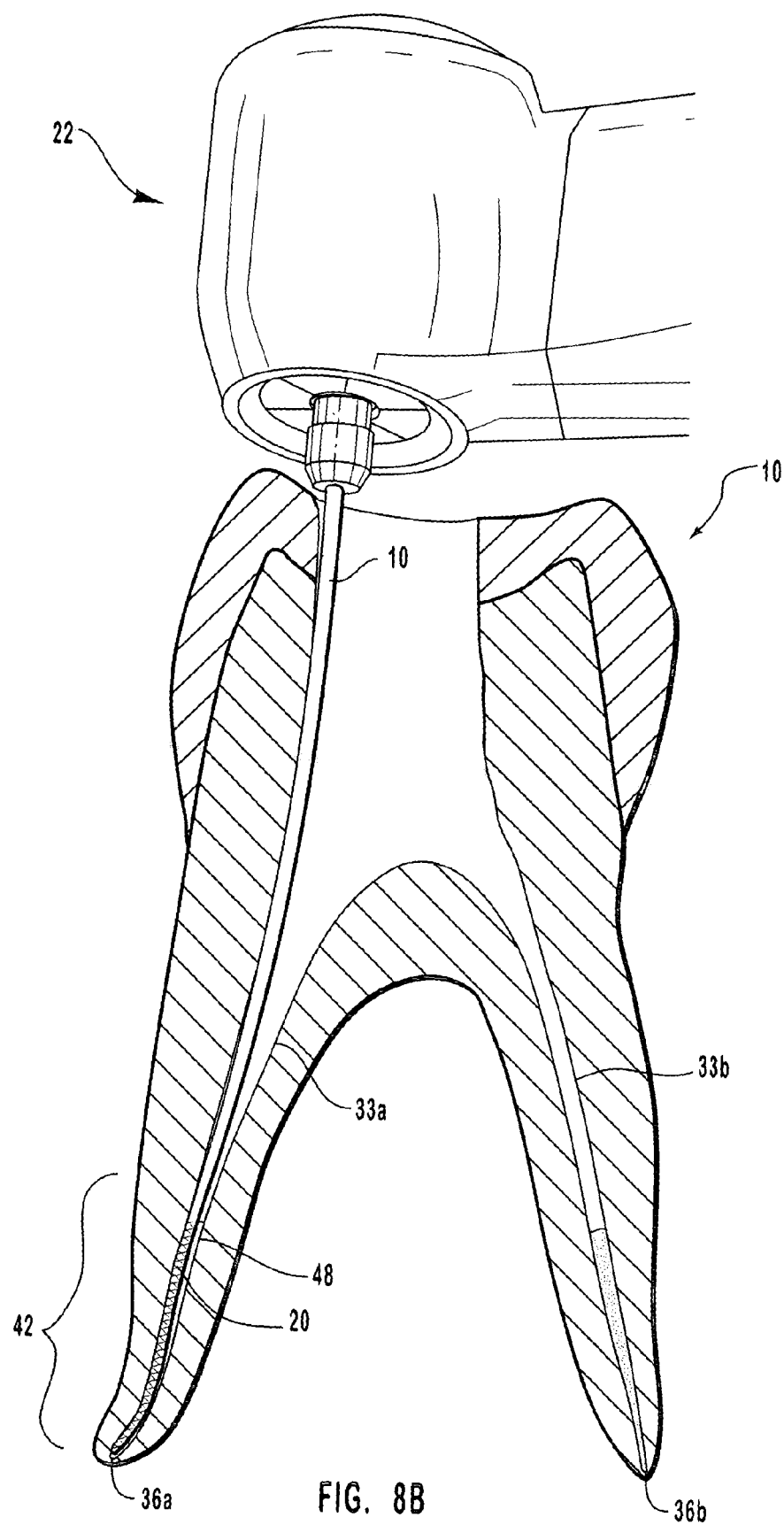
FIG. 8B illustrates cleaning and shaping of the apical third of the tooth of FIG. 8A using a reciprocating powered hand-piece according to another method of the present invention.

Once the pulp is removed from the middle portion 40, an apical file (e.g., file 10, 10', or 10" of FIGS. 2A, 2B, or 4, respectively) may be used to clean the apical portion 42 of root canal 33a, as shown in FIG. 8A or 8B. FIG. 8A illustrates manual use of apical file 10', while FIG. 8B illustrates use of apical file 10 with a powered hand piece, further illustrated and described below in conjunction with FIGS. 10A and 10B. The length of the apical file (e.g., 10, 10', or 10") is selected such that when the file is inserted into the root canal, the tip of the file can at least approximately reach apex 36a, and the abrading portion 20 of the apical file can substantially contact and clean pulp material 48 in the apical portion 42 of the root canal 33a. Such file lengths are typically within a range from about 8 mm to about 35 mm.

The shaft of apical files 10, 10', and 10" are made of a super-elastic material such that they can more easily take the contour of anatomical root canal 33. The super-elasticity of the shaft of apical files 10, 10', and 10" reduces the risk of ledging. Ledging can occur in root canals that have a substantial degree of curvature. The resilience in the material of more rigid endodontic files can cause the endodontic instrument to straighten. This straightening can cause the tip of the rigid instrument to aggressively abrade the root canal wall and form a ledge. Because the apical endodontic instruments used in the present invention are made of super-elastic materials, these instruments more easily follow the shape of the root canal and are less likely to cause ledging or other damage to the root canal wall.

The method of the present invention also includes reciprocating a super-elastic endodontic instrument such as apical file 10, 10', or 10" either in a reciprocating hand piece or manually to facilitate the removal of pulp 48 from the root canal. Because of the small spaces and delicacy of the apical portion 42 of root canal 33, the use of the apical file in a reciprocating manner reduces the duration of the endodontic procedure and produces more consistent removal of pulp and other endodontic tissue within the root canal.

The method of the present invention also includes reciprocating the endodontic instrument in desired degrees of rotation to prevent apical file 10, 10', or 10" from catching an edge and digging into the sidewall of root canal 33, thereby removing an undesirable amount of tissue. In an exemplary embodiment, apical file 10, 10', or 10" is inserted into root canal 33 and reciprocated in degrees of rotation less than about 120 degrees (e.g., about 60 degrees forward and about 60 degrees backwards) to remove the pulp from the apical portion 42. Reciprocating apical file 10, 10', or 10" in degrees of rotation less than about 120 degrees prevents apical file 10, 10', or 10" from catching an edge and removing excess endodontic tissue. As discussed above, more preferred degrees of rotation include about 90 degrees, about 70 degrees, and about 60 degrees of rotation.

By restricting the degree of rotation, the disadvantages of using a super-elastic apical file can be overcome. Surprisingly, by restricting rotation, the winding up effect caused by using a super-elastic material can be limited, but the apical file's ability to remove pulp and/or shape the root canal are not significantly diminished.

In an exemplary embodiment, the apical files 10, 10', or 10" have a number of cutting edges that are selected according to the degrees of rotation that are used to reciprocate the endodontic file. In one embodiment, the number of edges is sufficient such that the entire circumference of the endodontic file is abraded during a complete cycle of the endodontic instrument. For example, where the endodontic instrument is rotated a total of about 120 degrees, the number of cutting edges is preferably greater than or equal to 3 and the cutting edges are spaced such that a complete rotation of apical file 10, 10', or 10" can potentially abrade a complete circumferential path of surrounding pulp and/or endodontic tissue. In a more preferred embodiment, the endodontic instrument has at least 4 cutting edges and is rotated a total of less than about 90 degrees. More preferably the endodontic instrument has at least 6 cutting edges and is rotated a total of less than about 70 degrees and more preferably less than 60 degrees.

Figure 9A:
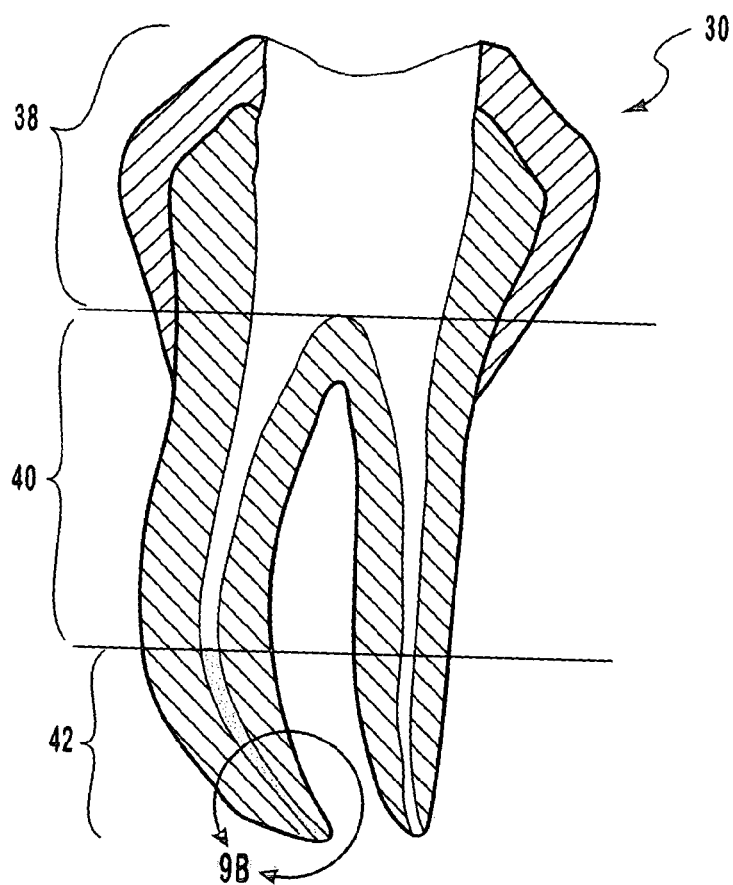
FIG. 9A illustrates a cross sectional view of the tooth of FIGS. 8A and 8B after cleaning of the apical portion of the tooth.
Figure 9B:
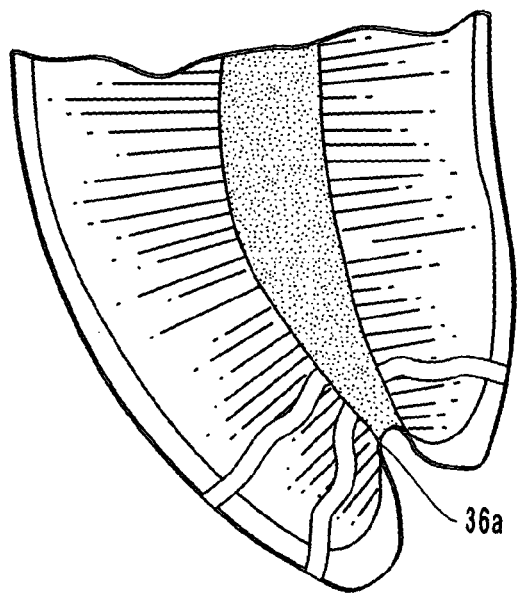
FIG. 9B illustrates a close up cross sectional view of the apical delta of FIG. 9A.

FIG. 9A illustrates a cross sectional view of the tooth 30 after cleaning of the apical portion 42 has been completed. As seen in FIG. 9B, the apex 36a of tooth 30 terminates in an apical delta.

Additional details relating to the top down method of cleaning a root canal can be found in Applicant's issued U.S. Pat. No. 6,746,245, entitled "Methods For Cleaning And Shaping Asymmetrical Root Canals In An Anatomical Fashion," which is incorporated herein by reference.

IV. Exemplary Powered Hand Pieces

Figure 10A:
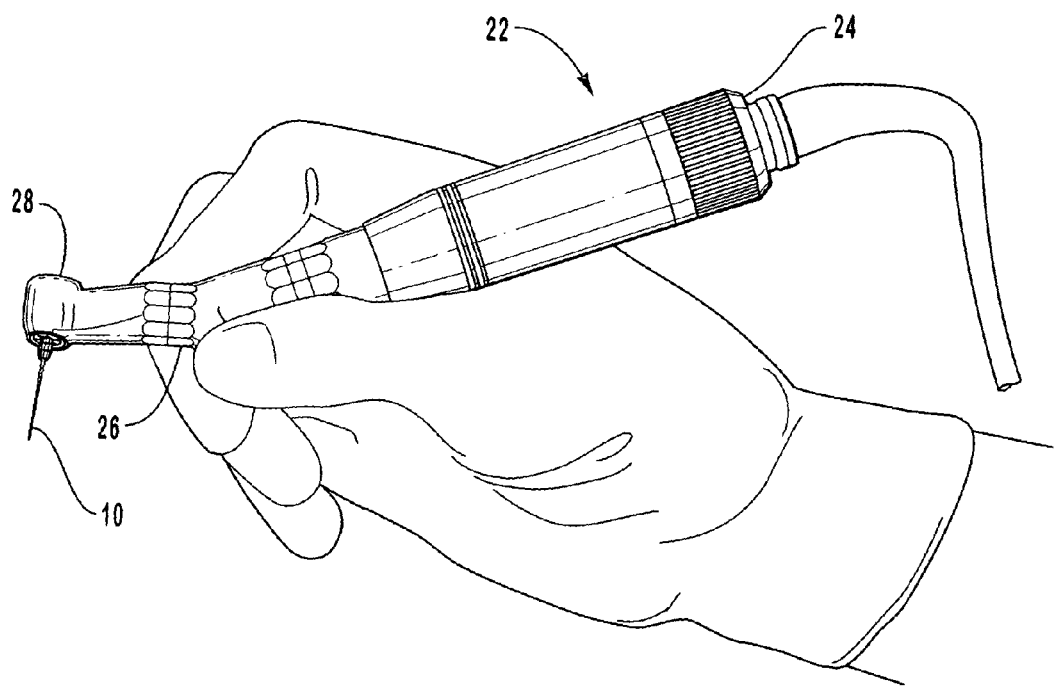
FIG. 10A illustrates an exemplary hand-piece for performing the exemplary method of FIG. 8B.
Figure 10B:
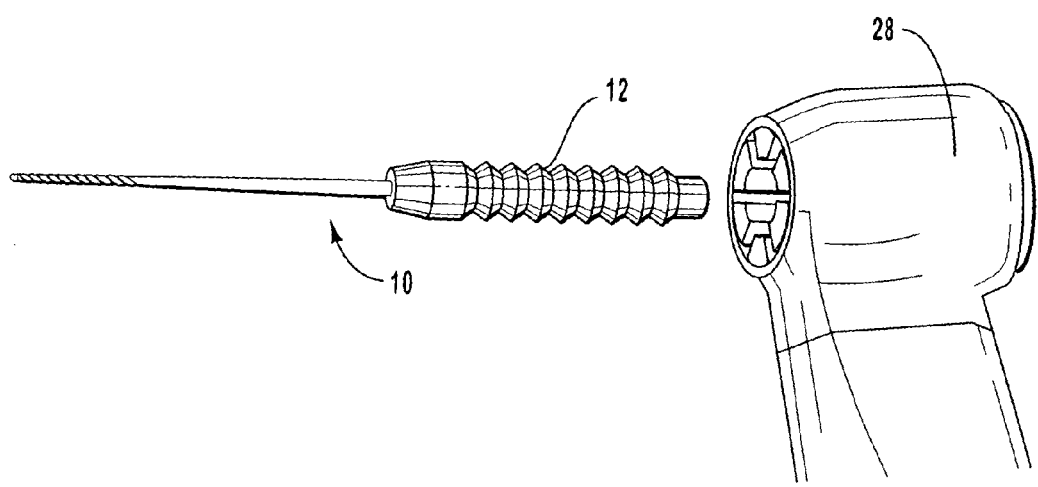
FIG. 10B illustrates insertion of the apical endodontic file into the hand-piece of FIG. 10A.

One method of reciprocating use involves attaching the apical file to a powered hand piece. FIG. 10A shows an exemplary embodiment of a powered hand piece 22 that can be used in such exemplary methods. Powered hand piece 22 includes a motor 24, a contra angle 26, and a hand piece head 28. Apical file 10 is attached to powered hand piece 22 through hand piece head 28. Insertion of the apical file 10 into hand piece head 28 is illustrated in FIG. 10B. Apical file 10 includes an alternative handle 12 useful in setting the working length of the apical file 10. Hand piece head 28 securely holds handle 12 of apical file 10 in a chuck of hand piece head 28 and rotates apical file 10 about its longitudinal axis.

In one embodiment, head 28 can be an integral component of a conventional contra angle, providing a drive train and gears necessary to rotate apical file 10 at a desired rate of rotation. Motor 24 can be electrically powered, air powered, or any similar mechanism that can drive the apical file in a controlled manner. Motor 24 is fastened to contra angle 26, by for example complementary threaded body parts and engages a contra angle drive train to rotate apical file 10.

In an exemplary embodiment, contra angle 26 includes a reciprocating mechanism that restricts the back and forth rotation of the apical file to a desired degree of rotation. Those skilled in the art are familiar with reciprocating mechanisms that use gears, cams, and other mechanical means to control the reciprocation of the apical file.

In an exemplary embodiment hand piece 22 is configured to rotate back and forth over an arc of about 120 degrees. Rotation of 120 degrees is obtained by rotating the apical file back about 60 degrees and forward about 60 degrees for a total arc of about 120 degrees. An arc of about 120 degrees can also be obtained by rotating apical file 10 back and forth in unequal degrees of rotation that sum to an arc of about 120 degrees. In a more preferred embodiment, the degree of rotation is restricted to an arc of less than about 90 degrees, more preferably an arc of less than about 70 degrees and most preferably an arc less than about 60 degrees.

In an alternative embodiment, the degree of rotation is controlled electronically by reversing the direction of rotation of the motor, rather than using mechanical means within the contra angle. In this embodiment, the hand piece is configured to rotate in a forward and a reverse direction. The degree of rotation is controlled by properly timing when the hand piece reverses direction. For example, where a total rotation of 90 degrees is desired, the hand piece can be set to reverse direction at about eight times the rate that it would take the apical file to complete one rotation. Using this technique, any of the above desired rotation arcs can be achieved.

V. Exemplary Kits

Figure 11A:
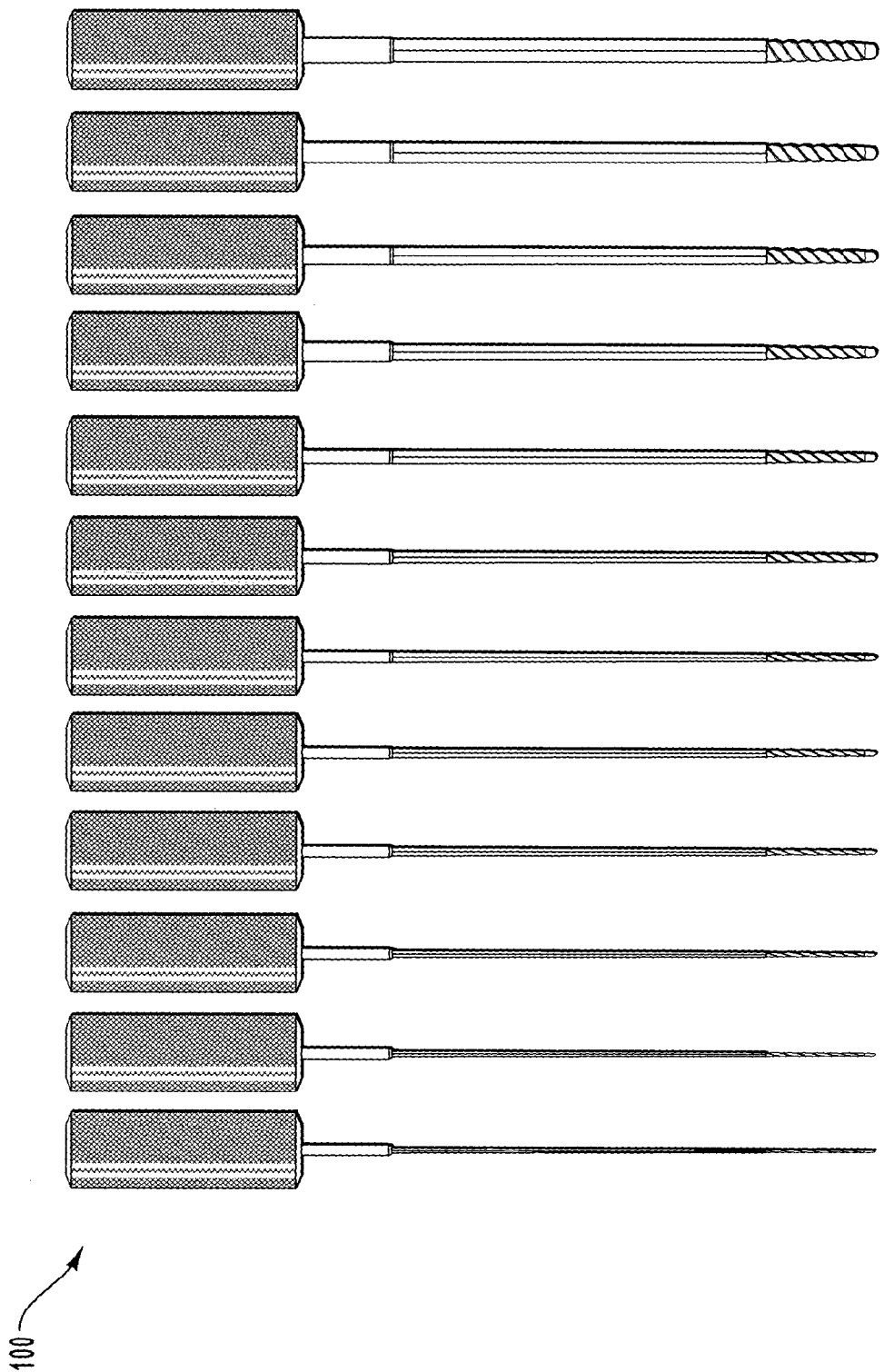
FIGS. 11A-11B illustrate exemplary kits of apical endodontic files for use in methods of the present invention.
Figure 11B:
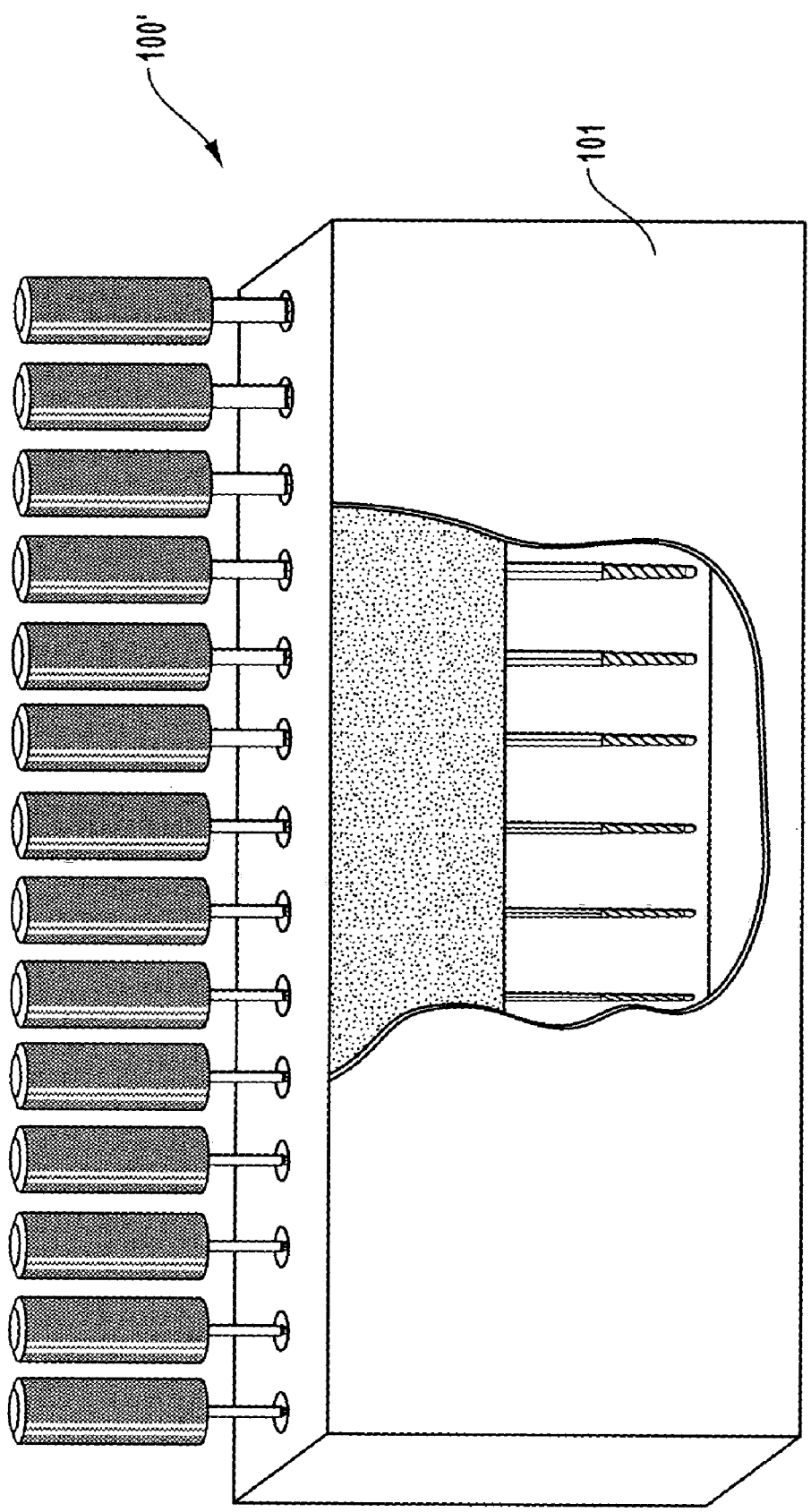

FIGS. 11A and 11B illustrate kits of apical endodontic files for use in the methods of the present invention. Kit 100 of FIG. 11A includes a plurality of apical endodontic files arranged by increasing diameter. FIG. 11B illustrates another kit 100' including apical endodontic files arranged by increasing diameter within a container 101. Exemplary included diameters (included within either kit) may include, but are not limited to, 0.08 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.7 mm, and 0.8 mm. The files may be of one or more lengths. Preferred lengths may include, but are not limited to 19 mm, 23 mm, 25 mm, 27 mm, and 30 mm. Although illustrated with apical files configured for manual use, it is to be understood that the kits may alternatively include apical files configured for use with a powered hand piece.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

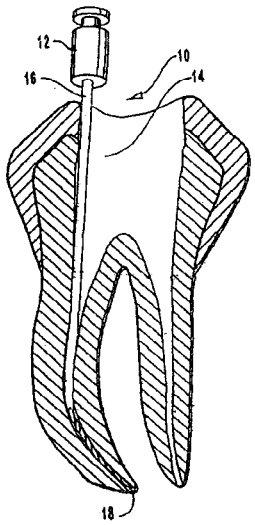

What is claimed is:

1. A method of cleaning the apical portion of a root canal of a tooth, the tooth having an operative coronal portion and a root canal portion, the root canal portion including an operative middle root canal portion and an apical root canal portion, the method comprising:
   providing an apical endodontic file comprised of a gripping portion and a thin, flexible, shaft extending from the gripping portion comprised of a super-elastic titanium-based material so as to be adaptable to a curvature of the root canal, wherein the shaft has a non-abrading portion proximal to the gripping portion and an abrading portion extending between a distal end of the shaft and the non-abrading portion, the abrading portion comprising less than about one-half the length of the shaft so that at least a portion of the non-abrading portion is positioned within the operative middle root canal portion when the abrading portion is positioned within the apical root canal portion, the apical endodontic file having greater flexibility than endodontic files used to clean the operative middle root canal portion;
   attaching the gripping portion of the apical endodontic file to a powered hand piece capable of moving the endodontic file in a reciprocating back and forth motion during use;
   inserting the apical endodontic file into the root canal of the tooth so that the non-abrading portion extends through the operative middle root canal portion and the abrading portion extends at least partially into the apical root canal portion; and
   cleaning the apical portion of the root canal by causing or allowing the powered hand piece to move the apical endodontic file in a back and forth reciprocating motion instead of continuous rotation in a single direction so that the apical abrading portion cuts or abrades tissue in the apical root canal portion without significantly cutting or abrading tissue in the operative middle root canal portion, the thin, flexible shaft adapting to the curvature of the root canal.

2. A method as recited in claim 1, wherein the abrading portion comprises less than about one-third the length of the shaft.

3. A method as recited in claim 1, wherein the abrading portion has a length less than about 6 mm.

4. A method as recited in claim 1, wherein the abrading portion has a diameter in a range of about 0.06 to about 1.4 mm.

5. A method as recited in claim 1, wherein the powered hand piece reciprocates the apical endodontic file in a back and forth motion so as to minimize or prevent risk of breakage of the shaft during use.

6. A method as recited in claim 5, wherein the powered hand piece reciprocates the apical endodontic file in back and forth rotations that total less than about 120 degrees per back and forth cycle.

7. A method as recited in claim 5, wherein the powered hand piece reciprocates the apical endodontic file in back and forth rotations that total less than about 90 degrees per back and forth cycle.

8. A method as recited in claim 5, wherein the powered hand piece reciprocates the apical endodontic file in back and forth rotations that total less than about 80 degrees per back and forth cycle.

9. A method as recited in claim 5, wherein the powered hand piece reciprocates the apical endodontic file in back and forth rotations that total less than about 70 degrees per back and forth cycle.

10. A method as recited in claim 5, wherein the powered hand piece reciprocates the apical endodontic file in back and forth rotations that total less than about 60 degrees per back and forth cycle.

11. A method as recited in claim 1, wherein the apical cutting portion has at least 3 helical cutting edges.

12. A method as recited in claim 1, wherein the apical cutting portion has at least 4 helical cutting edges.

13. A method as recited in claim 1, wherein the titanium-containing material further comprises nickel.

14. A method as recited in claim 13, wherein the titanium-containing material has a titanium content between about 20% and about 80%.

15. A method as recited in claim 13, wherein the titanium-containing material has a titanium content between about 30% and about 70%.

16. A method as recited in claim 13, wherein the titanium-containing material has a titanium content between about 40% and about 60%.

17. A method as recited in claim 1, wherein the titanium-containing material comprises niobium.

18. A method as recited in claim 1, wherein the titanium-containing material comprises at least one group IV transition metal, at least one group V transition metal, and oxygen.

19. A method as recited in claim 18, wherein the titanium-containing material has a composition in mole percent of 1Ti-12Ta-9Nb-3V-6Zr-1O or 1Ti-23Nb-0.7Ta-2Zr-1O.

20. A method as recited in claim 1, wherein the apical endodontic file is selected from a provided kit including a plurality of apical endodontic files having varying diameters.

21. A method as recited in claim 1, wherein the apical endodontic file is introduced into the root canal after first cleaning the operative middle root canal portion using one or more endodontic files that are more rigid than the apical endodontic file.

22. A method of cleaning a root canal of a tooth, the tooth having an operative coronal portion and a root canal portion, the root canal portion including an operative middle root canal portion, an apical root canal portion, and an apex of the root canal, the method comprising:
  cleaning the operative middle root canal portion of the tooth using one or more endodontic files and without cleaning down to the apex of the root canal;
  providing an apical endodontic file comprised of a gripping portion and a thin, flexible, shaft extending from the gripping portion comprised of a super-elastic nickel-titanium alloy so as to be adaptable to a curvature of the root canal, wherein the shaft has a non-abrading portion proximal to the gripping portion and an abrading portion extending between a distal end of the shaft and the non-abrading portion and having a length so that at least a portion of the non-abrading portion is positioned within the operative middle root canal portion when the abrading portion is positioned within the apical root canal portion, the apical endodontic file having greater flexibility than the one or more endodontic files used to clean the operative middle root canal portion;
  attaching the gripping portion of the apical endodontic file to a powered hand piece capable of moving the endodontic file in a reciprocating back and forth motion during use;
  inserting the apical endodontic file into the root canal of the tooth so that the non-abrading portion extends through the operative middle root canal portion and the abrading portion extends at least partially into the apical root canal portion; and
  cleaning the apical portion of the root canal by causing or allowing the powered hand piece to move the apical endodontic file in a back and forth reciprocating motion instead of continuous rotation in a single direction so that the apical abrading portion cuts or abrades tissue in the apical root canal portion without significantly cutting or abrading tissue in the operative middle root canal portion, the thin, flexible shaft adapting to the curvature of the root canal.

23. A method as recited in claim 22, wherein the abrading portion comprises less than about one-half the length of the shaft.

24. A method as recited in claim 22, wherein the abrading portion comprises less than about one-third the length of the shaft.

25. A method as recited in claim 22, wherein the abrading portion has a length less than about 6 mm.

26. A method of cleaning a root canal of a tooth, the tooth having an operative coronal portion and a root canal portion, the root canal portion including an operative middle root canal portion, and an apical root canal portion, the method comprising:
  providing a tooth in which the operative middle root canal portion has been cleaned and in which at least a portion of the apical root canal portion has not been cleaned;
  providing an apical endodontic file comprised of a gripping portion and a thin, flexible, shaft extending from the gripping portion comprised of a super-elastic nickel-titanium alloy so as to be adaptable to a curvature of the root canal, wherein the shaft has a non-abrading portion proximal to the gripping portion and an abrading portion extending between a distal end of the shaft and the non-abrading portion and having a length so that at least a portion of the non-abrading portion is positioned within the operative middle root canal portion when the abrading portion is positioned within the apical root canal portion, the abrading portion having a length less than about 6 mm and comprising less than about one-half the length of the shaft;
  attaching the gripping portion of the apical endodontic file to a powered hand piece capable of moving the endodontic file in a reciprocating back and forth motion during use;
  inserting the apical endodontic file into the root canal of the tooth so that the non-abrading portion extends through the operative middle root canal portion and the abrading portion extends at least partially into the apical root canal portion; and cleaning the apical portion of the root canal by causing or allowing the powered hand piece to move the apical endodontic file in a back and forth reciprocating motion instead of continuous rotation in a single direction so that the apical abrading portion cuts or abrades tissue in the apical root canal portion without significantly cutting or abrading tissue in the operative middle root canal portion, the thin, flexible shaft adapting to the curvature of the root canal.

* * * * *

UNITED STATES PATENT AND TRADEMARK OFFICE
CERTIFICATE OF CORRECTION

PATENT NO. : 7,980,853 B2  
APPLICATION NO. : 11/175239  
DATED : July 19, 2011  
INVENTOR(S) : Francesco Riitano Page 1 of 3

It is certified that error appears in the above-identified patent and that said Letters Patent is hereby corrected as shown below:

Replace Title Page with the attached Title Page.

<u>Drawings</u>
Sheet 1, replace Figure 1 with the figure depicted below, wherein the second instance of "16" has been changed to --18--

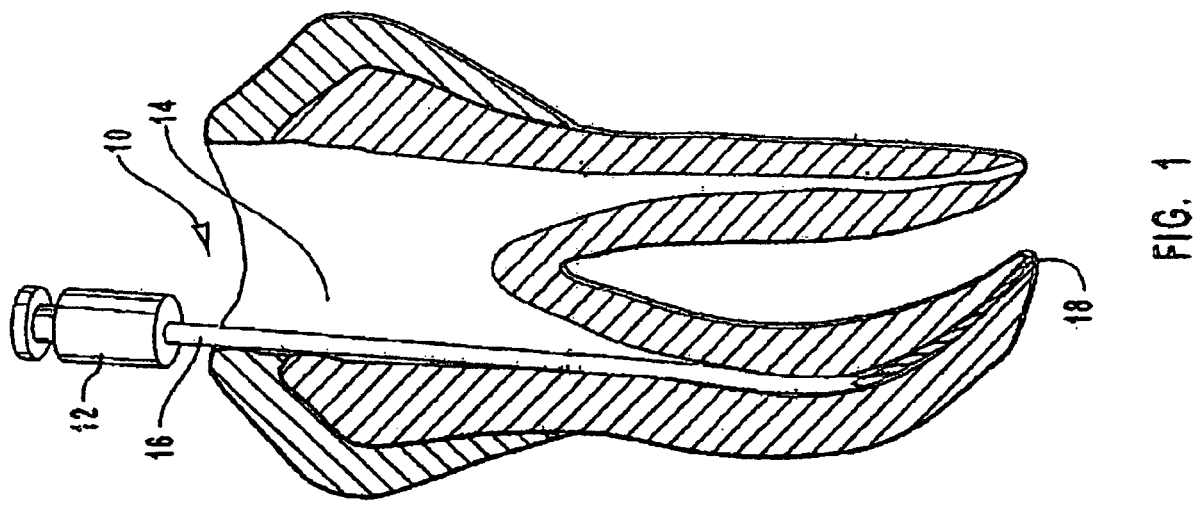

Sheet 8, replace Figure 8B with the figure depicted below, wherein the second instance of "10" has been changed to --30--

Signed and Sealed this  
Fourth Day of October, 2011

David J. Kappos  
*Director of the United States Patent and Trademark Office*

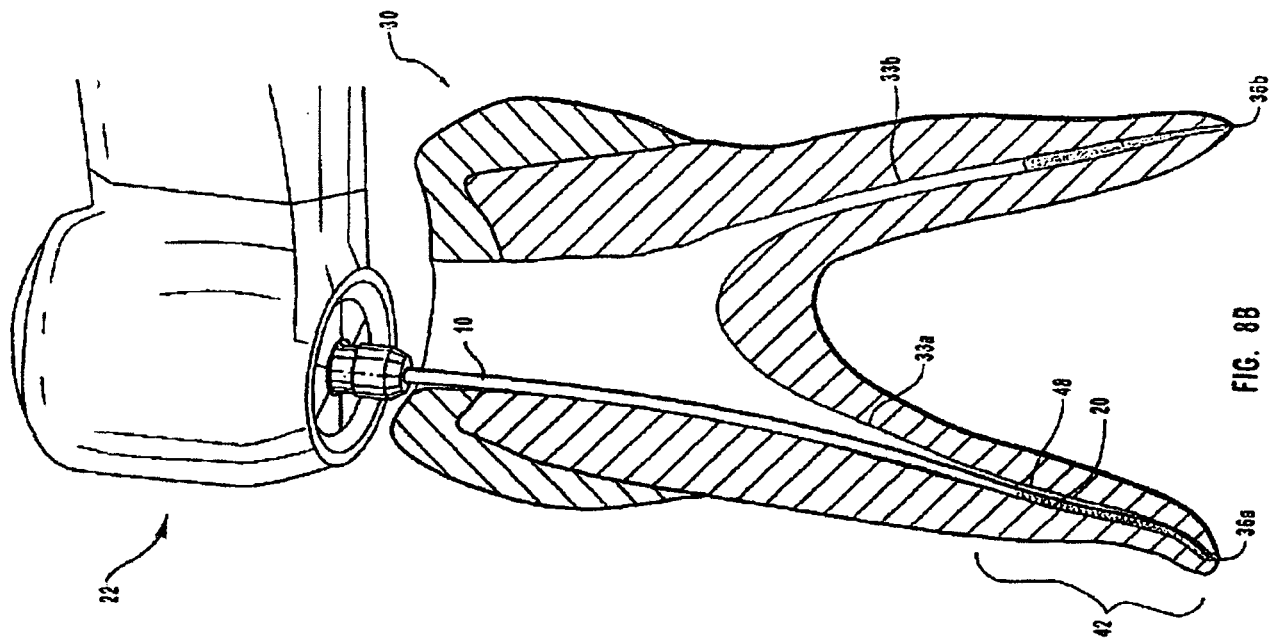
Column 2
Line 11, change "in" to --is--
Line 13, change "know" to --known--
Column 5
Line 25, change "In a one" to --In one--
Column 6
Line 1, change "about mole percent" to --about 15 mole percent--

CERTIFICATE OF CORRECTION (continued)

(12) United States Patent
Riitano

(10) Patent No.: US 7,980,853 B2
(45) Date of Patent: Jul. 19, 2011

(54) METHODS FOR APICAL PREPARATION USING ENDODONTIC INSTRUMENTS MADE OF SUPER-ELASTIC ALLOYS

(75) Inventor: Francesco Riitano, Soverato (IT)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 11/175,239

(22) Filed: Jul. 6, 2005

(65) Prior Publication Data

US 2007/0009850 A1 Jan. 11, 2007

(51) Int. Cl.
A61C 5/02 (2006.01)
(52) U.S. Cl. ....................................... 433/224
(58) Field of Classification Search ............... 433/102, 433/81, 224
See application file for complete search history.

(56) References Cited

U.S. PATENT DOCUMENTS

| | | | | |
|---|---|---|---|---|
| 3,578,745 | A | * | 5/1971 | Garnier et al. ............ 433/102 |
| 4,544,356 | A | | 10/1985 | Gardella et al. |
| 4,611,508 | A | * | 9/1986 | Roane ............... 76/24.1 |
| 4,889,487 | A | | 12/1989 | Lovaas |
| 5,380,200 | A | * | 1/1995 | Heath et al. ............ 433/102 |
| 5,653,590 | A | * | 8/1997 | Heath et al. ............ 433/102 |
| 5,857,852 | A | * | 1/1999 | Garman ............... 433/102 |
| 5,915,964 | A | | 6/1999 | Walia |
| 5,938,440 | A | | 8/1999 | McSpadden |
| 6,217,335 | B1 | * | 4/2001 | Riitano et al. ............ 433/224 |
| 6,293,795 | B1 | | 9/2001 | Johnson |
| 6,390,819 | B2 | | 5/2002 | Riitano |
| 6,431,863 | B1 | | 8/2002 | Sachdeva et al. |
| 6,520,774 | B1 | | 2/2003 | Mays |
| 6,585,513 | B2 | | 7/2003 | Fischer |
| 6,746,245 | B2 | | 6/2004 | Riitano et al. |
| 2001/0016309 | A1 | * | 8/2001 | Riitano ............... 433/224 |
| 2002/0137008 | A1 | | 9/2002 | McSpadden et al. |
| 2003/0211442 | A1 | * | 11/2003 | Abel ............... 433/102 |
| 2004/0058298 | A1 | | 3/2004 | Brava et al. |
| 2004/0121283 | A1 | * | 6/2004 | Mason ............... 433/102 |

OTHER PUBLICATIONS

Riitano, F., Anatomic Endodontic Technology (AET)—a crown-down root canal preparation technique: basic concepts operative procedure and instruments; International Endodontic Journal, vol. 38, pp. 575-587 (2005).

Serota, K. et al., Predictable Endodontic Success: The Hybrid Approach—Part I—Oral Health, vol. 93(5), pp. 41-48 (2003).

Serota, K. et al., Predictable Endodontic Success: Part II—Microstructural Replication—Oral Health, vol. 12(93), pp. 36-41 (2003).

Ponti, T. et al., Canal-centering ability of two rotary file systems, J. Endod., vol. 28(4), pp. 283-286 (Apr. 2002).

* cited by examiner

Primary Examiner — Cris L Rodriguez
Assistant Examiner — Sunil K Singh
(74) Attorney, Agent, or Firm — Workman Nydegger

(57) ABSTRACT

The apical third of a root canal is cleaned and/or shaped during a root canal procedure with an endodontic file made from a titanium-based alloy either by reciprocating manual use or by using a reciprocating powered hand piece. The titanium-based endodontic file has super-elastic properties that allow it to be very flexible and strong. The endodontic file is rotated in the apex of a root canal in degrees of rotation less than 120 degrees. By restricting the degree of rotation, excessive cutting by the endodontic file is kept to a minimum. The use of elastic alloys of titanium help prevent ledging or other damage to the root canal wall that may be caused using rigid apical files made of stainless steel.

26 Claims, 12 Drawing Sheets